United States Patent [19]

Kado et al.

[11] Patent Number: 5,211,178
[45] Date of Patent: May 18, 1993

[54] METHOD AND APPARATUS FOR SYNCHRONOUSLY DETECTING A MAGNETOCARDIOGRAM AND METHOD AND APPARATUS FOR SYNCHRONOUSLY ADDING MAGNETOCARDIOGRAMS

[75] Inventors: Hisashi Kado, Kashiwa; Tomoaki Ueda, Kyoto, both of Japan

[73] Assignees: Agency of Industrial Science & Technology; Daikin Industries, both of Japan

[21] Appl. No.: 766,349

[22] Filed: Sep. 27, 1991

[30] Foreign Application Priority Data

Sep. 30, 1990 [JP] Japan .................................. 2-262015

[51] Int. Cl.$^5$ .......................................... A61N 5/0472
[52] U.S. Cl. .................................................. 128/700
[58] Field of Search .................... 128/653.1, 695, 696, 128/700; 364/413.05, 413.06

[56] References Cited

U.S. PATENT DOCUMENTS

| 4,204,225 | 5/1980 | Mistretta | 128/695 |
| 4,403,184 | 9/1983 | Witt et al. | 128/695 |
| 4,934,374 | 6/1990 | Ostlund et al. | 128/695 |
| 4,951,674 | 8/1990 | Zanakis | 128/653.1 |
| 4,996,479 | 2/1991 | Hoenig | 128/653.1 |
| 5,033,472 | 7/1991 | Sato et al. | 128/700 |

FOREIGN PATENT DOCUMENTS 1503742 8/1989 U.S.S.R. .............................. 128/696

OTHER PUBLICATIONS

Odehnal et al., "Cryogenics" vol. 18, No. 7, Jul. 1978, pp. 427–431.
Cohen et al "Applied Physics Letters" vol. 16, No. 7, Apr. 1970, pp. 278–280.

Primary Examiner—William E. Kamm
Attorney, Agent, or Firm—Beveridge, DeGrandi, Weilacher

[57] ABSTRACT

Cross-correlation values representative of cross-correlation of an electrocardiogram pulse with a rectangular pulse window which consists of a negative rectangular pulse, a positive rectangular pulse and a negative rectangular pulse are obtained. An R-wave of the electrocardiogram is detected by a peak of the cross-correlation values is detected. Then a magnetocardiogram in synchronism with the R-wave of the electrocardiogram is detected. Magnetocardiograms corresponding to individual cycles of a magnetocardiogram can be added as required.

8 Claims, 11 Drawing Sheets

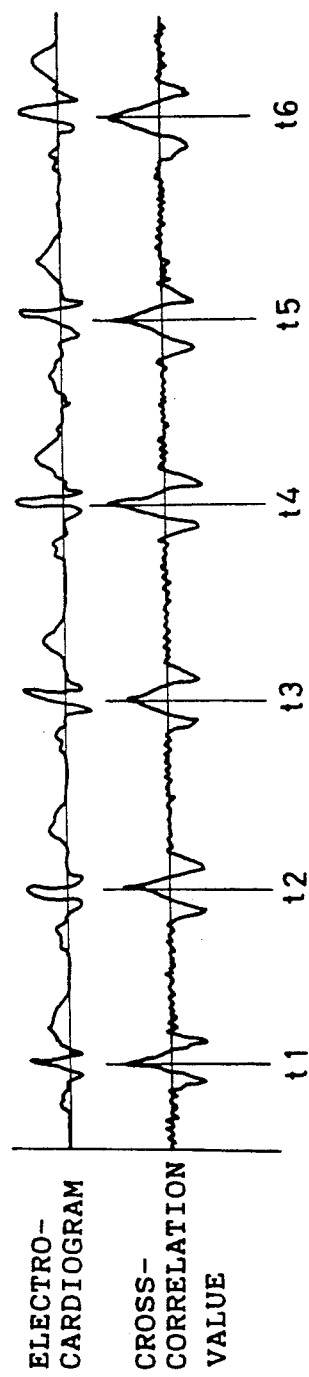

CROSS-CORRELATION VALUE

METHOD AND APPARATUS FOR SYNCHRONOUSLY DETECTING A MAGNETOCARDIOGRAM AND METHOD AND APPARATUS FOR SYNCHRONOUSLY ADDING MAGNETOCARDIOGRAMS

BACKGROUND OF THE INVENTION

The present invention relates to a method and apparatus for synchronously detecting a magnetocardiogram. The present invention also relates to methods and apparatus for synchronously adding magnetocardiograms. More particularly, the present invention relates to a method and an apparatus for detecting a magnetocardiogram in synchronism with a Q-R-S group of an electrocardiogram, the magnetocardiogram being measured by a superconducting quantum interference device magnetic flux meter including a superconducting quantum interference device (hereinafter referred to as a SQUID). The present invention also relates to methods and apparatus for adding magnetocardiograms corresponding to individual cycles of a magnetocardiogram in synchronism with a Q-R-S group of an electrocardiogram, the magnetocardiogram being measured by a SQUID magnetic flux meter including a SQUID.

It is known that a SQUID is capable of detecting magnetic flux with extremely high sensitivity. Wi&h attention to this characteristic, a SQUID is applied to various apparatus which are used in various technical fields. When an object of magnet flux measurement is a living organism, it is strongly desired that magnetic flux is measured without an invasive procedure. Therefore, it is proposed that a magnetocardiogram is measured using a SQUID magnetic flux meter.

Conventionally a method for measuring an electrocardiogram is generally employed so as to diagnose diseases of the heart. For example, the method is insufficient for estimating a position of a part of the heart which is to be singled out during an operation, that is, satisfactory estimation of a position is not obtained. The reason for insufficient estimation is that accurate wave forms of electrocardiograms cannot be obtained and only almost uniform wave forms of electrocardiograms ere accordingly obtained at all measurement times because an electrocardiogram is an indirect measurement method, and an electrocardiogram depends on relative positions, sizes, electric conductivities and the like of the anatomy between the heart and the surface of the body, and other internal organs, may vary a fair amount according to the person to be measured. To overcome the disadvantage mentioned above, a method for directly pricking or contacting a needle electrode or meshed electrode to the heart is employed so as to estimate an accurate position in singling out a portion of the heart. Disadvantages arise in that a time period for opening a patient's thorax for an abdominal operation is lengthened and a required time period for an operation on the heart is also lengthened. Therefore, measurement without invasion for estimating an accurate position in a short period of time for singling out a portion of the heart, is strongly demanded.

A dc-SQUID is being widely used because two Josephson junctions having similar characteristics can be obtained due to improvements in thin film manufacturing engineering in recent years. Measuring a magnetocardiogram using a SQUID magnetic flux meter is carried out for trial by taking the demand into consideration. When magnetocardiograms are to be measured, the measured magnetocardiograms differ from one another due to individuals and measurement situations. Seizing a magnetic field corresponding to a situation of heart at a desired time is accordingly difficult. It is proposed that a magnetic field is easily seized by determining a trigger level for triggering the magnetocardiogram with an R-wave of an electrocardiogram by using the electrocardiogram as a triggering signal and by detecting the magnetocardiogram in synchronism with the electrocardiogram. It is also proposed that magnetocardiograms corresponding to individual cycles of a magnetocardiogram are added and averaged in synchronism with an R-wave of an electrocardiogram so as to improve a signal to noise ratio (hereinafter referred to as S/N ratio).

The electrocardiogram includes characteristic variations due to living organisms, as is mentioned above, and a measured electrocardiogram includes a characteristic fluctuation (1/t) refer to FIG. 8, for example). That is, the electrocardiogram may include not only variations in proper shapes and amplitude of Q-R-S groups but also an offset which is convoluted to a ground level due to myoelectric potential. Therefore, when a trigger level is simply determined which is shown by a dashed line in FIG. 9(A), disadvantages arise in that a magnetocardiogram may be triggered with T-waves of an electrocardiogram and that shifting in synchronization may occur by several to several tens of milliseconds as is shown in FIG. 9(A). Consequently, magnetocardiograms corresponding to individual cycles of a magnetocardiogram cannot be added in synchronism accurately, thereby the improvement of the S/N ratio to a predetermined value cannot be performed. Specifically, a level of an R-wave is lowered while levels of a P-wave and T wave are relatively raised by performing the synchronous addition of magnetocardiograms as is shown in FIG. 9(C).

It may be proposed that a peak position of the Q-R-S group is to be detected. Then, similar disadvantages as in above-mentioned arise because a shape of the R-wave greatly varies in the neighbouring portion to the peak Of the R-wave with respect to the zero-crossing center of the Q-R-S group as is shown in FIG. 9(B).

Furthermore, a disadvantage arises in that determination of the triggering level is difficult because an amplitude of the T wave may be great due to a guiding method of an electrocardiogram or differences between persons.

SUMMARY OF THE INVENTION

It is an object of the present invention to eliminate the influence of fluctuation in an electrocardiogram.

It is another object of the present invention to synchronously detect a magnetocardiogram with high accuracy.

It is a further object Of the present invention to synchronously add magnetocardiograms corresponding to individual cycles of a magnetocardiogram with high accuracy.

To perform the objects above-mentioned, a method for synchronously detecting a magnetocardiogram comprises the steps of;

obtaining cross-correlation values representative of cross-correlation of an electrocardiogram with a rectangular pulse window which consists of a negative rectangular pulse ave, a positive rectangular pulse wave and a negative rectangular pulse wave, in this order, detecting Q-R-S groups of the electrocardiogram based on the obtained cross-correlation values, and detecting a magnetocardiogram in synchronism with the detected Q-R-S groups.

When this method is employed, the greatest cross-correlation values are obtained corresponding to the R-waves of the electrocardiogram by obtaining cross-correlation values representative of cross-correlation of the electrocardiogram with the rectangular pulse window consisting of the negative rectangular pulse wave, the positive rectangular pulse wave and the negative rectangular pulse wave, because the Q-R-S groups of the electrocardiogram vary by a negative level, a positive level and a negative level in this order. Therefore, a magnetocardiogram is synchronously detected with high accuracy and with elimination of the influence of fluctuation in the electrocardiogram by detecting a magnetocardiogram supposing the times corresponding to the greatest cross-correlation values as the midtimes of the corresponding Q-R-S groups.

To perform the objects above-mentioned, a method for synchronously adding magnetocardiograms comprises the steps of;

obtaining cross-correlation values representative of cross-correlation of an electrocardiogram with a rectangular pulse window which consists of a negative rectangular pulse, a positive rectangular pulse and a negative rectangular pulse, in this order, detecting Q-R-S groups of the electrocardiogram based on the obtained cross correlation values, and adding magnetocardiograms corresponding to individual cycles of a magnetocardiogram in synchronism with the detected Q-R-S groups.

When this method is employed, the greatest cross-correlation values are obtained corresponding to the R-waves of the electrocardiogram by obtaining cross-correlation values representative of cross-correlation of the electrocardiogram with the rectangular pulse window consisting Of the negative rectangular pulse wave, the positive rectangular pulse wave and the negative rectangular pulse wave, because the Q-R-S groups of the electrocardiogram vary by a negative level, a positive level and a negative level, in this order. Therefore, magnetocardiograms corresponding to individual cycles of a magnetocardiogram are synchronously added with high accuracy and with elimination of the influence of fluctuation in the electrocardiogram so as to improve the S/H ratio, by adding magnetocardiograms corresponding to individual cycles of a magnetocardiogram supposing the times corresponding to the greatest cross-correlation values as the midtimes of the corresponding Q-R-S groups.

It is preferable that the time width ratio of the negative rectangular pulse wave, positive rectangular pulse wave and negative rectangular pulse wave of the rectangular pulse window is 1:2:1.

When this method is employed, cross-correlation values corresponding to P-waves and T-waves are nearly 0.

It is also preferable that the amplitudes of the negative rectangular pulse waves of the rectangular pulse window are "−1" and the amplitude of the positive rectangular pulse wave of the rectangular pulse window is "1".

When this method is employed, cross-correlation values are obtained by performing only cumulative addition and reduction, thereby processings can be simplified.

To perform the objects above-mentioned, an apparatus for synchronously detecting a magnetocardiogram comprises;

cross-correlation means for obtaining cross-correlation values representative of cross-correlation of an electrocardiogram with a rectangular pulse window which consists of a negative rectangular pulse wave, a positive rectangular pulse wave and a negative rectangular pulse wave, in this order, R-wave detection means for detecting R-waves of the electrocardiogram based on the obtained cross-correlation values, and magnetocardiogram detection means for detecting a magnetocardiogram in synchronism with the detected R-waves.

When this apparatus is employed, cross-correlation values representative of cross-correlation of the electrocardiogram with the rectangular pulse window are obtained by the cross-correlation means, then the R-waves are detected by the R-wave detection means based on the greatest cross-correlation values, because the Q-R-S groups of the electrocardiogram vary by a negative level, a positive level and a negative level, in this order. Therefore, a magnetocardiogram is synchronously detected by the magnetocardiogram detection means with high accuracy and with elimination of the influence of fluctuation in the electrocardiogram, by detecting a magnetocardiogram supposing the times corresponding to the nearest cross-correlation values as the midtimes of the corresponding Q-R-S groups.

To perform the objects above-mentioned, an apparatus for synchronously adding magneto-cardiograms comprises;

cross-correlation means for obtaining cross-correlation values representative of cross-correlation of an electrocardiogram with a rectangular pulse window which consists of a negative rectangular pulse wave, a positive rectangular pulse wave and a negative rectangular pulse wave, R-wave detection means for detecting R-waves of the electrocardiogram based on the obtainer cross-correlation values, and addition means for adding magnetocardiograms corresponding to individual cycles of a magnetocardiogram in synchronism with the detected R-waves.

When this apparatus is employed, cross-correlation values representative of cross-correlation of the electrocardiogram with the rectangular pulse window are obtained by the cross-correlation means, then the R-Waves are detected by the R-wave detection means based on the greatest cross-correlation values, because the Q-R-S groups of the electrocardiogram vary by a negative level, a positive level and a negative level, in this order. Therefore, magnetocardiograms corresponding to individual cycles of a magnetocardiogram are synchronously added by the addition means with high accuracy and with elimination of the influence of fluctuation in the electrocardiogram, by adding magnetocardiograms corresponding to individual cycles of a magnetocardiogram supposing the times corresponding to the greatest cross-correlation values as the midtimes of the corresponding Q-R-S groups.

It is preferable that the time width ratio of the negative rectangular pulse wave, positive rectangular pulse wave and negative rectangular pulse wave of the rectangular pulse window is 1:2:1.

When this method is employed, cross-correlation values corresponding to P-waves and T-waves are nearly 0.

It is also preferable that the amplitudes of the negative rectangular pulse waves of the rectangular pulse window are "−1" and the amplitude of the positive rectangular pulse wave of the rectangular pulse window is "1".

When this method is employed, cross-correlation values are obtained by performing only cumulative addition and reduction, thereby processings can be simplified.

These and other objectives, features and advantages of the invention will be more readily understood upon consideration of the preset invention, in conjunction with the accompanying drawings.

DETAILED DESCRIPTION OF THE PREFERRED EMBODIMENTS

Figure 1:
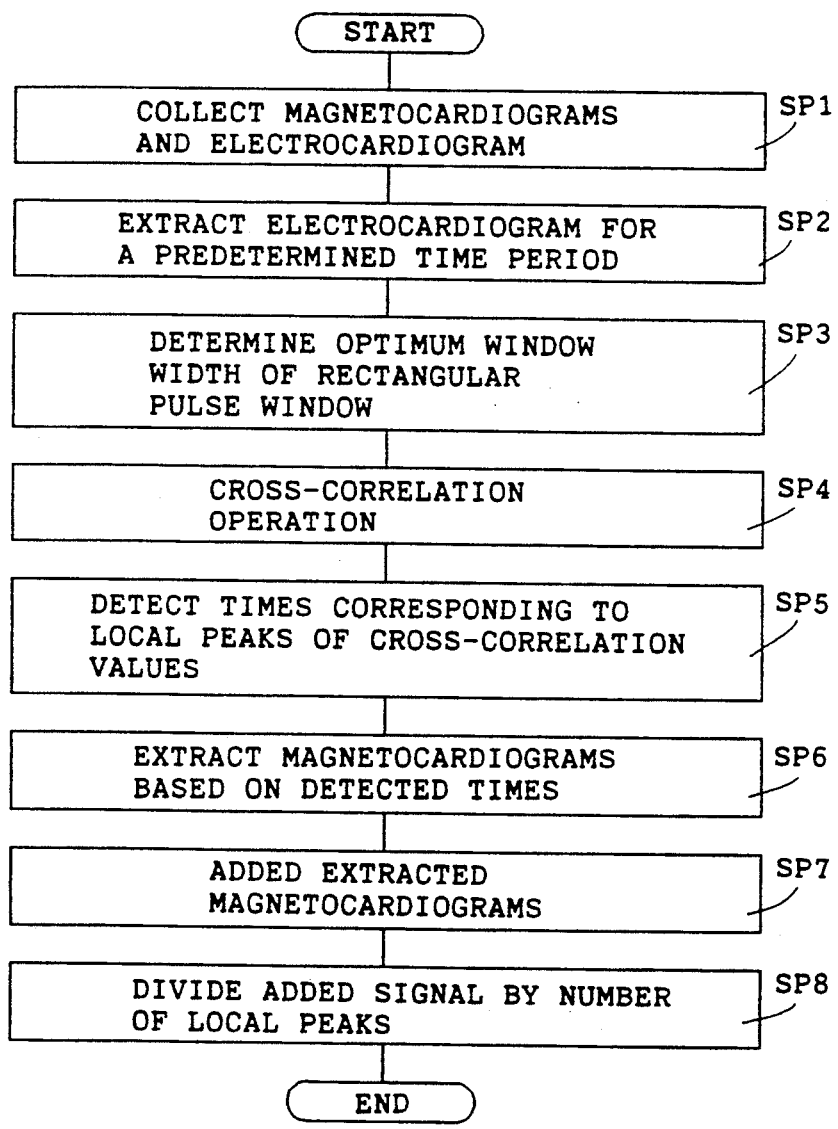
FIG. 1 is a flowchart illustrating a method for synchronously adding magnetocardiograms according to the present invention.

FIG. 1 is a flowchart illustrating a method for synchronously adding magnetocardiograms according to the present invention.

Figure 2:
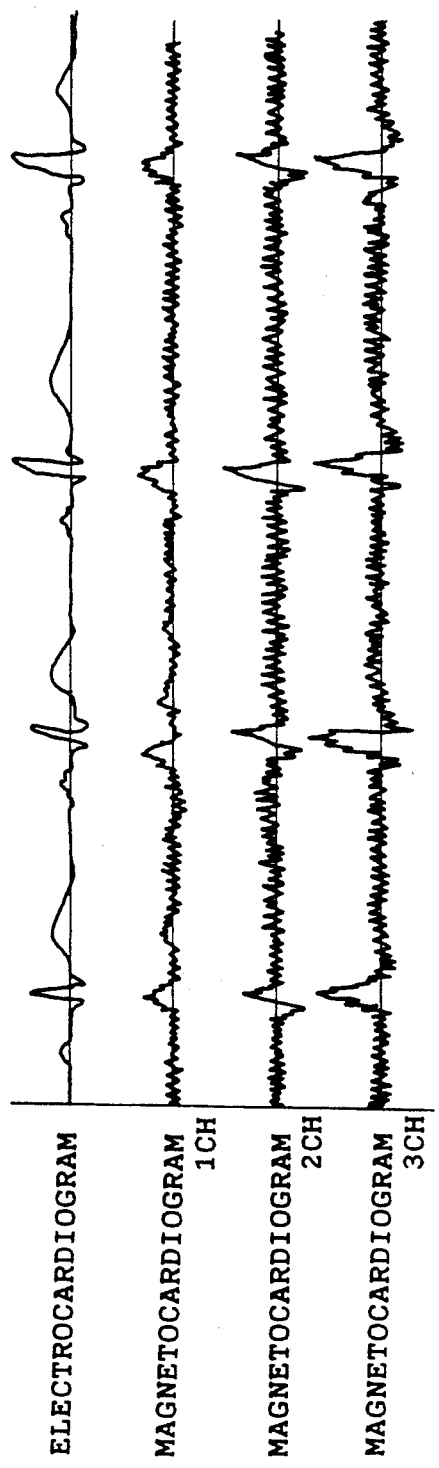
FIG. 2(A) is a diagram illustrating an electrocardiogram and magnetocardiograms.
FIG. 2(B) is a diagram illustrating a rectangular pulse window.
FIG. 2(C) is a diagram illustrating an electrocardiogram and cross-correlations thereof.
FIG. 2(D) is a diagram illustrating synchronous addition operations.
FIG. 2(E) is a diagram illustrating an added signal.
FIG. 2(F) is a diagram illustrating an added and averaged signal.
Figure 2:
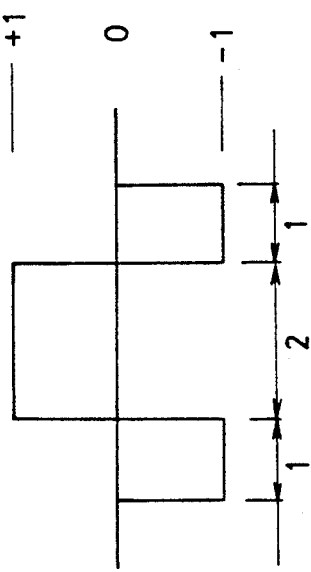
Figure 2:
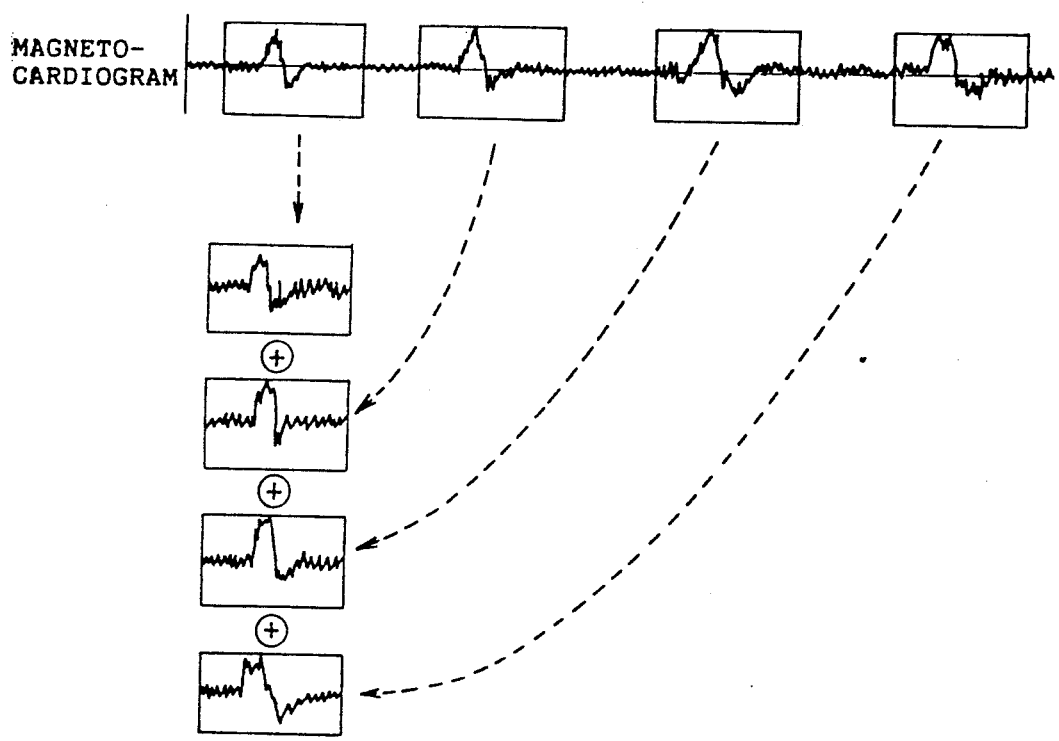
Figure 2:
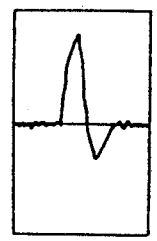
Figure 2:
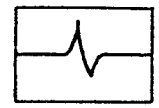

In step SP1, magnetocardiograms for plural channels together with an electrocardiogram are collected as is shown in FIG. 2(A). In step SP2, an electrocardiogram for a predetermined time period (for example, for several seconds) is extracted. In step SP3, the width of a rectangular pulse window (refer to FIG. 2(B)) is determined to be an optimum width based on the extracted electrocardiogram, the rectangular pulse window consisting of a negative rectangular pulse wave, a positive rectangular pulse wave and a negative rectangular pulse wave, in this order, and the time width of the positive rectangular pulse wave being twice that f the negative rectangular pulse wave. In step SP4, to the extracted electrocardiograms are applied cross-correlation operations with the rectangular pulse window for an entire time period so as to Obtain cross-correlation values (refer to FIG. 2(C)). In step SP5, times corresponding to local peaks of cross-correlation values are detected. In step SP6, magnetocardiograms are extracted for predetermined begins with respect to corresponding times, corresponding to local peaks (for example from times prior to times corresponding to local peaks by 300 milliseconds to times after times corresponding to local peaks by 600 milliseconds)(refer to FIG. 2(D)). In step 7, the extracted magnetocardiograms are added for corresponding channels as is shown in FIG. 2(D) so as to obtain an added signal (refer to FIG. 2(E)). In step 8, the obtained added signal is divided by the number of local peaks so as to obtain a synchronously added and averaged signal of the magnetocardiogram (refer to FIG. 2(F)).

Figure 3:
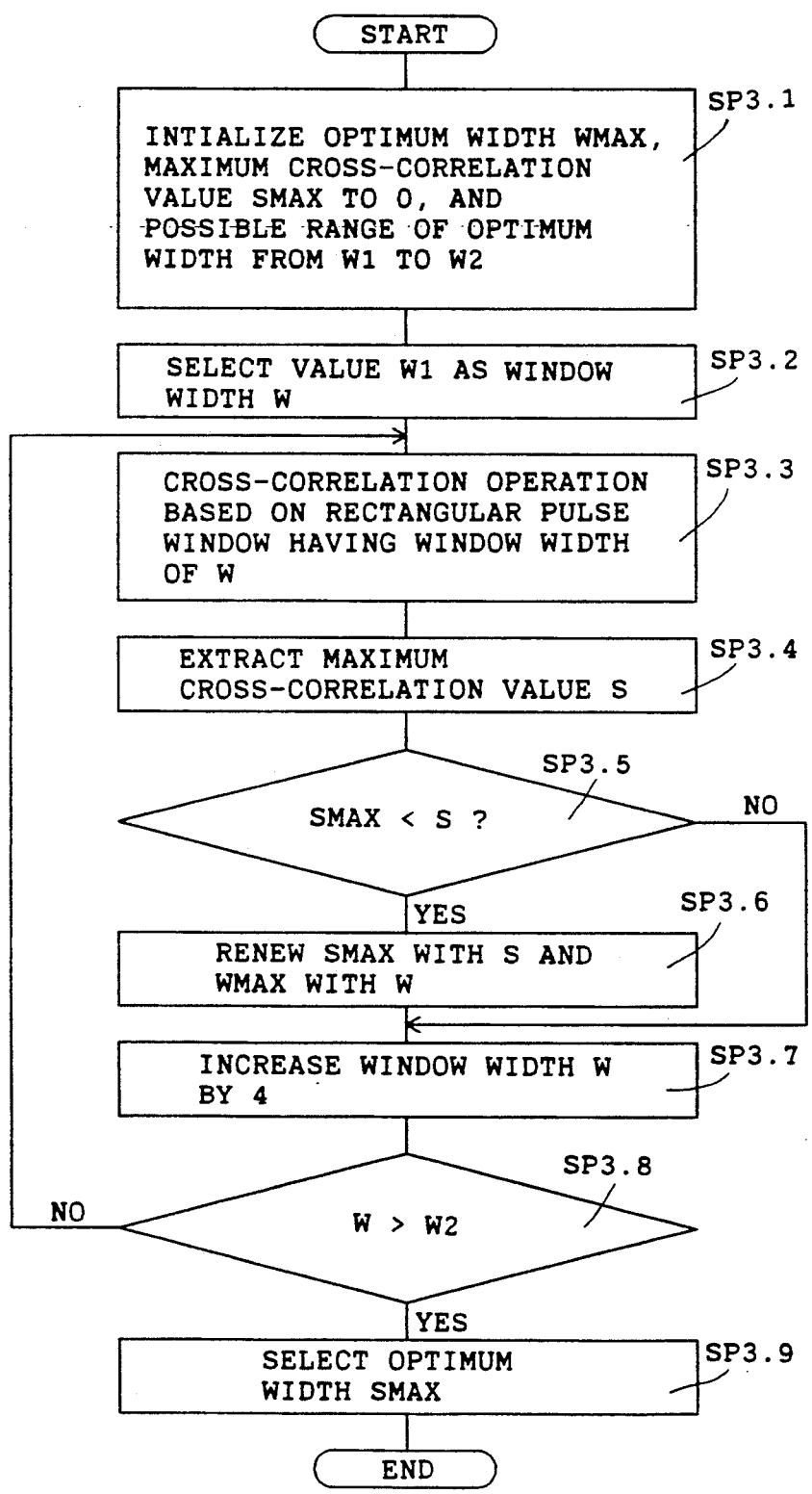
FIG. 3 is a flowchart illustrating operations for determining the time width of a rectangular pulse window.

FIG. 3 is a flowchart illustrating processing in step SP3 in detail.

In step SP3.1, an optimum width Wmax of the rectangular pulse window and a maximum cross-correlation value Smax are initialized to 0 and a possible range of the optimum width is determined from W1 to W2. In step SP3.2, the value W1 is selected as a window width W of the rectangular pulse window. In step SP3.3, a cross-correlation operation is carried out for the rectangular pulse window having the window width of W and the electrocardiogram for a predetermined tine period. In step SP3.4, the maximum value S of the cross-correlation values is extracted. In step SP3.5, it is judged whether or not the extracted maximum value S is greater than the maximum cross correlation value Smax. When it is judged in step SP3.5 that the extracted maximum value S is greater than the maximum cross correlation value Smax, in step SP3.6, the maximum cross-correlation value Smax and the optimum width Wmax are renewed based on the extracted maximum value S and the selected window width W. In step SP3.7, the window width W is increased by 4 samples. In step SP3.8, it is judged whether or not the increased window width W exceeds the upper limit W2 of the possible range. When it is judged in step SP3.8 that the increased window width W does not exceed the upper limit W2, the processing in step SP3.3 is carried out again. When it is judged in step SP3.5 that the extracted maximum value S is not greater than the maximum cross-correlation value Smax, the processing in step SP3.7 is carried out. When it is judged in step SP3.8 that the increased window width W exceeds the upper limit W2, in step SP3.9, the optimum width Wmax which has already been obtained is selected as the optimum width of the rectangular pulse window, then the series of processings are finished.

When the series of processings are carried out, magnetocardiograms are detected in synchronism with the Q-R-S groups of the electrocardiogram even though the electrocardiogram includes characteristic variations due to living organisms, by performing cross-correlation with the electrocardiogram and the rectangular pulse window, and by obtaining times corresponding to local peaks of the cross-correlation values. Thereafter, the magnetocardiograms are added in synchronism with the Q-R-S groups of the electrocardiogram by determining the obtained times as standard times. Therefore, the disadvantage that the level of the R-wave is lowered while the levels of the P-wave and the T-wave are relatively raised, is prevented from occurring. Consequently, a magnetocardiogram with a high S/N ratio is obtained by dividing the synchronously added magnetocardiogram by an addition number of the magnetocardiograms. As a result, a position singled Out for an operation on the heart can be estimated with high accuracy based on the finally obtained magnetocardiograms for plural channels.

A position singled out for an operation on the heart can be estimated with high accuracy without a division operation when the addition numbers for plural channels are the same. The window width of the rectangular pulse window may be previously determined and fixed to a predetermined width.

Figure 4:
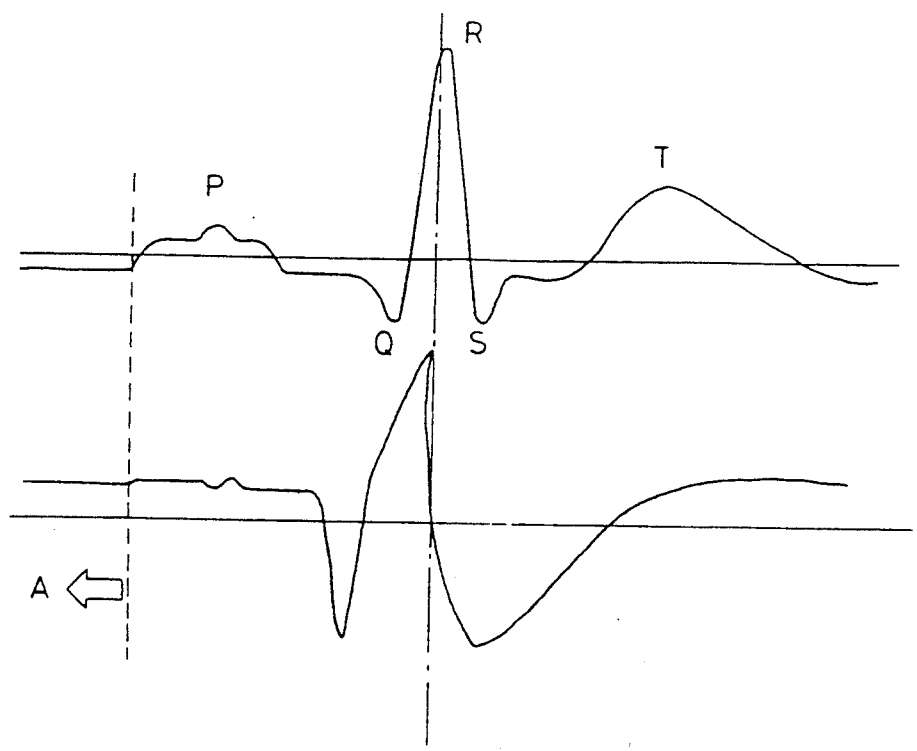
FIG. 4 is a diagram useful in understanding a ground level detection operation for canceling direct current offset.

A magnetocardiogram is generally convoluted with a direct current offset (hereinafter referred to as dc-offset). When the dc-offset is required to be canceled, it is sufficient that an added and averaged value of the magnetocardiogram be used for a time period prior to the occurrence of the P-wave of the electrocardiogram (for example, a time period prior to the occurrence of the P-wave by more than 20 milliseconds, and the time period corresponds to a region A in FIG. 4) after the synchronously adding and averaging operation for the magnetocardiogram has been carried our, and that an offset canceling operation is carried out by determining the added and averaged value as the ground level.

Apparatus Embodiment

Figure 5:
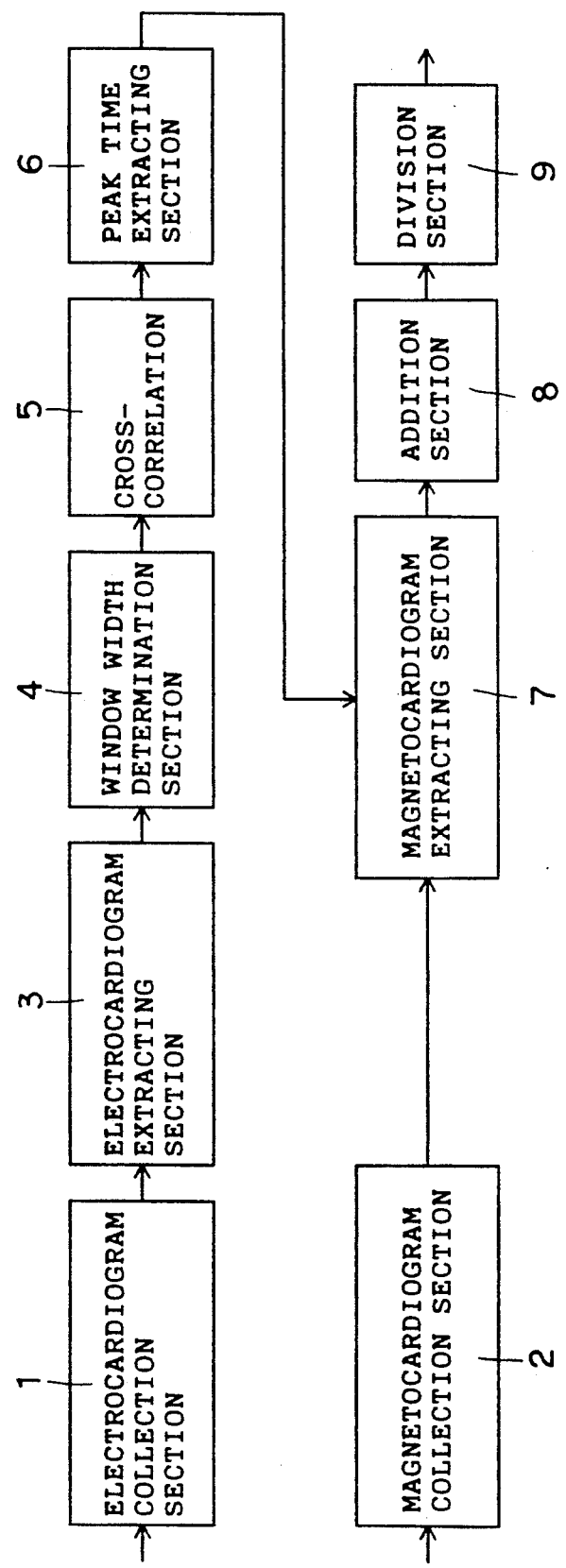
FIG. 5 is a block diagram showing an embodiment of an apparatus for synchronously adding magnetocardiograms according to the present invention.

FIG. 5 is a block diagram showing an embodiment of an apparatus for synchronously adding magnetocardiograms according to the present invention.

The apparatus comprises;

an electrocardiogram collection section 1 for collecting an electrocardiogram, magnetocardiogram collection section 2 for plural channels for collecting magnetocardiograms respectively, each magnetocardiogram collection section including a SQUID magnetic flux meter.

an electrocardiogram partially extracting section 3 for extracting an electrocardiogram for a predetermined time period from the collected electrocardiogram, a window width determination section 4 for determining the optimum width of a rectangular pulse window based on the extracted electrocardiogram, the rectangular pulse window consisting of a negative rectangular pulse wave, a positive rectangular pulse wave and a negative rectangular pulse wave, in this order, and the time width of the positive rectangular pulse wave being twice that of a negative rectangular pulse wave, a cross-correlator 5 for performing a cross-correlation operation with the electrocardiogram extracted by the electrocardiogram partially extracting section 3 and the rectangular pulse window for an entire time period so as to obtain cross-correlation values, a peak time extracting section 6 as an R-wave detection means for extracting times corresponding to local peaks of the cross-correlation values, a magnetocardiogram extracting section 7 for extracting magnetocardiograms of corresponding channels within predetermined time periods which are determined with respect to the corresponding extracted times as standards, an addition section 8 for adding the extracted magnetocardiograms of corresponding channels to obtain addition results, and a division section 9 for dividing the addition results by the number of extracted times.

Figure 6:
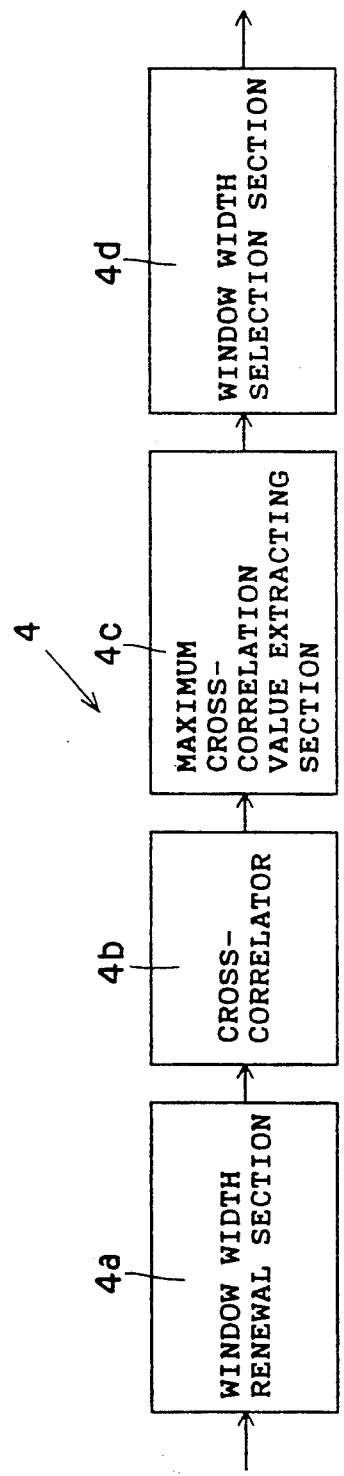
FIG. 6 is a block diagram showing a width determining section.

The window width determination section 4 is shown in FIG. 6 and comprises;

a window width renewal section 4a for renewing window width sequentially, a cross-correlator 4b for performing cross-correlation operation with the electrocardiogram extracted for a predetermined time period based on a rectangular pulse window with a renewed window width, a maximum cross-correlation value extracting section 4c for extracting the maximum cross-correlation value from the obtained cross-correlation values, and a window width selection section 4d for extracting the maximum cross-correlation value from all maximum cross-correlation values which are extracted by the maximum cross-correlation value extracting section 4c at every renewal of window width, and for selecting the window width corresponding to the extracted maximum cross-correlation value as the window width of a rectangular pulse window.

Operation of the apparatus for synchronously adding magnetocardiograms having the arrangement above-mentioned is as follows.

An electrocardiogram is collected by the electrocardiogram collection section 1, then a part of the collected electrocardiogram is extracted by the electrocardiogram partially extracting section 3. The window width determination section 4 determines a window width which causes a cross-correlation value to be the maximum cross-correlation value. Thereafter, the cross-correlator 5 performs the cross-correlation operation with the collected electrocardiogram for the entire extent based on the rectangular pulse window which has the determined window width, and the peak time extracting section 6 extracts times corresponding to local peaks of the cross-correlation values.

Magnetocardiograms for plural channels are collected by the corresponding magnetocardiogram collection section 2. The magnetocardiogram extracting section 7 extracts magnetocardiograms of corresponding channels within predetermined time periods which are determined with respect to the corresponding extracted times as standards. The addition section 8 adds the extracted magnetocardiograms for corresponding channels to obtain addition results. The division section 9 divides the addition results by the number of the extracted times so as to obtain a synchronously added and averaged signal for the magnetocardiogram. The synchronously added and averaged signal of the magnetocardiogram has an extremely improved S/N ratio. As a result, a position singled out for operation on the heart can be estimated with high accuracy, based on the finally obtained magnetocardiograms for plural channels.

A position singled out for operation of heart can be estimated with high accuracy without a division operation when the addition numbers for plural channels are the same. The window width Of the rectangular pulse window may be previously determined and fixed to a predetermined width.

A magnetocardiogram is generally convoluted with a dc-offset. When the dc-offset is required to be canceled, it is sufficient that an added and averaged value of the magnetocardiogram be used for a time period prior to the occurrence of the P-wave of the electrocardiogram after the synchronously adding and averaging operation for the magnetocardiogram has been carried out, and that an offset canceling operation is carried out by determining the added and averaged value as the ground level.

Figure 7:
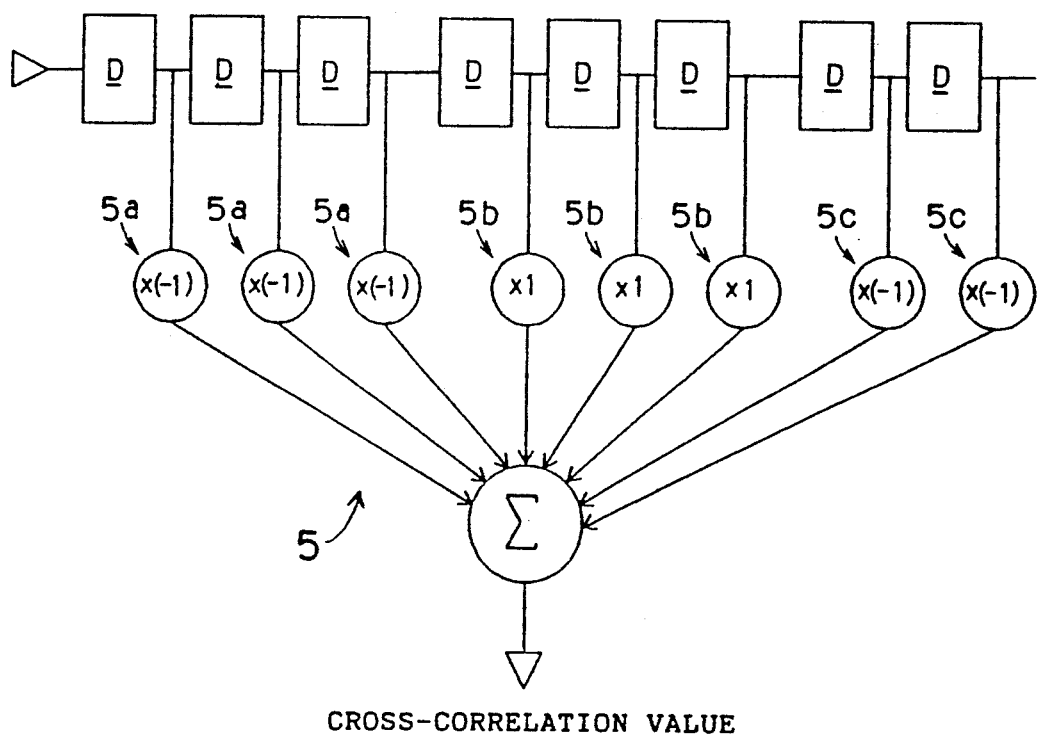
FIG. 7 is a block diagram showing a cross-correlator.
Figure 8:
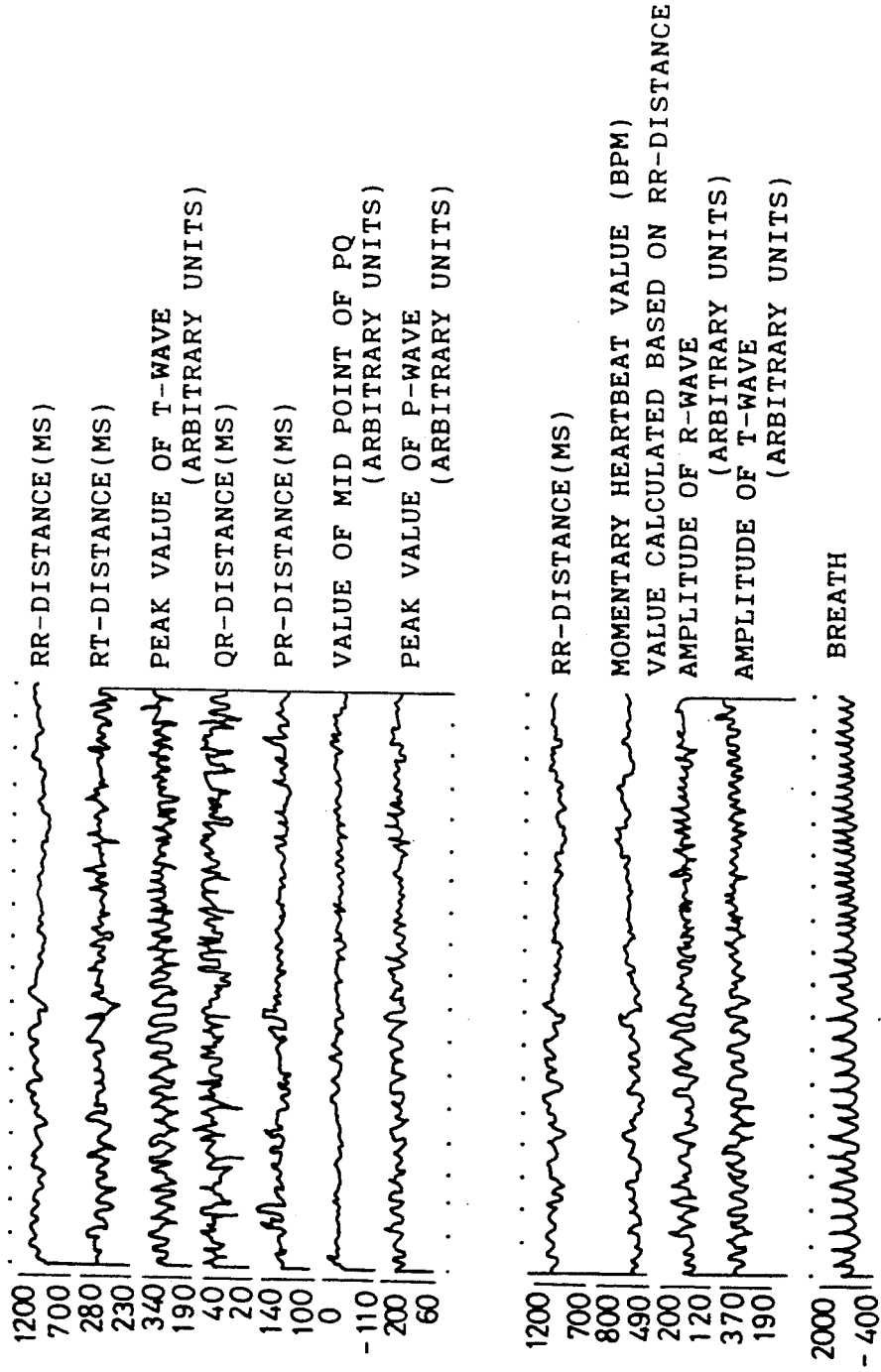
FIG. 8 is a measurement sample of an electrocardiogram and breath monitoring.
Figure 9:
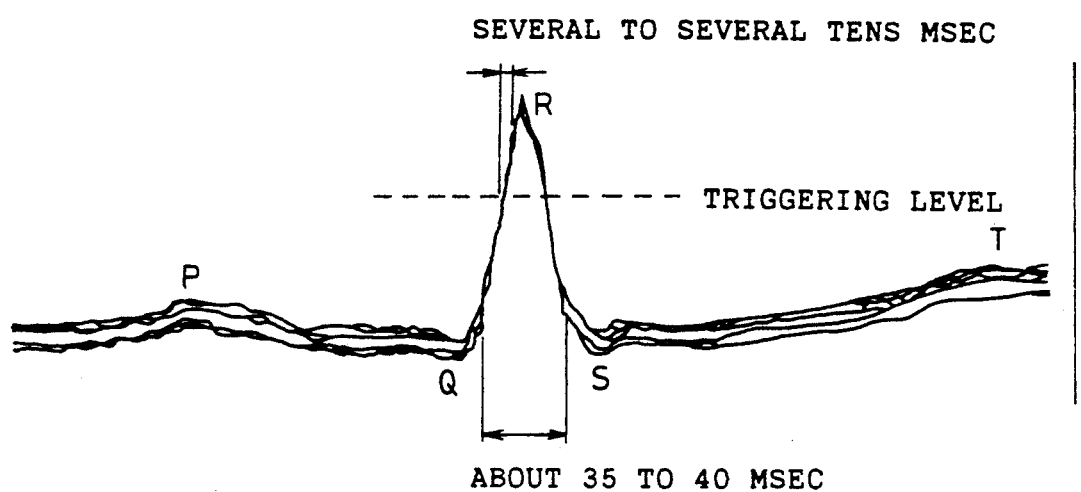
FIGS. 9(A), 9(B), 9(C) are diagrams useful in understanding the disadvantages of a conventional method for synchronously adding magnetocardiograms.
Figure 9:
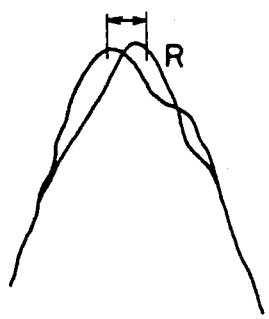
Figure 9:
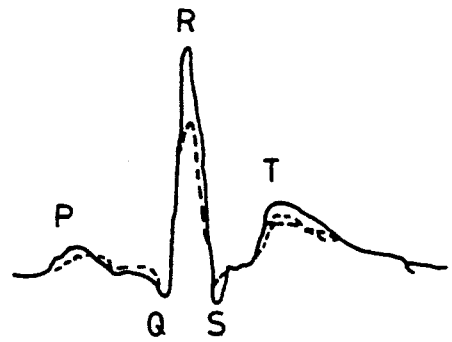

FIG. 7 is a block diagram showing the cross-correlator 5.

The cross-correlator 5 comprises plural delay circuits D interconnected in serial, each delay circuit D delaying an electrocardiogram by a predetermined time period, a cumulative addition section $\Sigma$, plural inverters 5a which are illustrated in FIG. 7 as multiplication circuits for multiplying the value of "$-1$", for receiving output signals from some upper-stream-side delay circuits D and for supplying output signals therefrom to the cumulative addition section $\Sigma$, plural inverters 5c which are illustrated in FIG. 7 as multiplication circuits for multiplying the value of "$-1$, for receiving output signals from some lower-stream-side delay circuits D and for supplying output signals therefrom to the cumulative addition section $\Sigma$, and plural converters 5b which are illustrated in FIG. 7 as multiplication circuits for multiplying the value of "1" for receiving output signals from the rest of delay circuits D and for supplying output signals therefrom to the cumulative addition section $\Sigma$.

When this cross-correlator 5 is employed, cross-correlation values are obtained without a multiplication operation by determining the amplitude of the positive rectangular pulse wave of the rectangular pulse window to be "1" and by determining the amplitude of the negative rectangular pulse wave of the rectangular pulse window to be "$-1$".

The method and apparatus for synchronously detecting magnetocardiogram and the method and apparatus for synchronously adding magnetocardiograms are not limited to the embodiments mentioned above. The methods and apparatus may determine the time width ratio Of the negative rectangular pulse wave and positive rectangular pulse wave of the rectangular pulse window to a value other than 1:2. The methods and apparatus may determine the amplitudes of the rectangular pulse waves of the rectangular pulse window to arbitrary values.

The terms and expressions which have been employed are used as terms or description and not of limitation, and there is no intention, in the use of such terms and expressions, to exclude equivalents of the features shown and described, or portions thereof, it being recognized that various modifications are possible within the scope of the invention as claimed.

What is claimed is:

1. A method for synchronously detecting a magnetocardiogram comprising the steps of:
receiving an electrocardiogram signal;
receiving a magnetocardiogram signal;
determining a rectangular pulse window signal which consists of a negative rectangular pulse wave, a positive rectangular pulse wave and a negative rectangular pulse wave, in this order;
cross-correlating the electrocardiogram signal with the rectangular pulse window signal to obtain a cross-correlation values signal;
detecting Q-R-S groups of the electrocardiogram signal based on the obtained cross-correlation values signal; and
detecting a portion of the magnetocardiogram signal which is in synchronism with the detected Q-R-S groups.

2. A method for synchronously adding magnetocardiograms comprising the steps of:
receiving a electrocardiogram signal;
receiving magnetocardiogram signals;
determining a rectangular pulse window signal which consists of a negative rectangular pulse, a positive rectangular pulse and a negative rectangular pulse, in this order;
cross-correlating the electrocardiogram signal with the rectangular pulse window signal to obtain a cross-correlation values signal;
detecting Q-R-S groups of the electrocardiogram based on the obtained cross-correlation values signal; and
adding magnetocardiogram cycle portions which are in synchronism with the detected Q-R-S groups.

3. A method for synchronously adding magnetocardiograms as set forth in claim 2, wherein a time width ratio of the negative rectangular pulse wave, the positive rectangular pulse wave, and the negative rectangular pulse wave of the rectangular pulse window signal is 1:2:1.

4. A method for synchronously adding magnetocardiograms as set forth in claim 2, wherein the amplitudes of the negative rectangular pulse waves of the rectangular pulse window are "$-1$" and the amplitude of the positive rectangular pulse wave of the rectangular pulse window is "1".

5. An apparatus for synchronously detecting a magnetocardiogram comprising:
means for receiving an electrocardiogram signal;
means for determining a rectangular pulse window signal which consists of a negative rectangular pulse wave, a positive rectangular pulse wave and a negative rectangular pulse wave, in this order;
cross-correlation means for cross-correlating a received electrocardiogram signal with a determined rectangular pulse wave signal to obtain a cross-correlation values signal;
R-wave detection means for detecting R-waves of a received electrocardiogram signal based on an obtained cross-correlation values signal; and
magnetocardiogram detection means for detecting a magnetocardiogram signal in synchronism with detecting R-waves.

6. An apparatus for synchronously adding magnetocardiograms comprising:
means for receiving an electrocardiogram signal;
means for receiving magnetocardiogram signals;
means for determining a rectangular pulse window signal which consists of a negative rectangular pulse wave, a positive rectangular pulse wave and a negative rectangular pulse wave in this order;
cross-correlation means for cross-correlating a received electrocardiogram signal with a determined rectangular pulse wave signal to obtain a cross-correlation values signal;
R-wave detection means for detecting R-waves of a received electrocardiogram signal based on an obtained cross-correlation values signal; and
addition means for adding received magnetocardiogram signals corresponding to individual cycles of a magnetocardiogram signal in synchronism with detected R-waves.

7. An apparatus for synchronously adding magnetocardiograms as set forth in claim 6, wherein a time width ratio of the negative rectangular pulse wave, the positive rectangular pulse wave and the negative rectangular pulse wave of said rectangular pulse window signals is 1:2:1.

8. An apparatus for synchronously adding magnetocardiograms as set forth in claim 6, wherein amplitudes of the negative rectangular pulse waves of the rectangular pulse window are "−1" and an amplitude of the positive rectangular pulse wave of the rectangular pulse window is "1".

* * * * *